(12) United States Patent  
Maleev

(10) Patent No.: US 8,502,977 B1  
(45) Date of Patent: Aug. 6, 2013

(54) ANGULAR RESOLVED SPECTROSCOPIC SCATTEROMETER

(75) Inventor: Ivan Maleev, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 449 days.

(21) Appl. No.: 12/791,446

(22) Filed: Jun. 1, 2010

(51) Int. Cl.  
*G01J 3/46* (2006.01)

(52) U.S. Cl.  
USPC .............................. 356/369; 356/326; 356/73

(58) Field of Classification Search  
USPC ..................................... 356/364–369, 326, 73  
See application file for complete search history.

(56) References Cited

U.S. PATENT DOCUMENTS

| | | | | |
|---|---|---|---|---|
| 5,872,630 | A  * | 2/1999 | Johs et al. | 356/369 |
| 7,463,369 | B2 * | 12/2008 | Wack et al. | 356/625 |
| 7,471,386 | B2 * | 12/2008 | Neiss et al. | 356/301 |
| 7,483,133 | B2 * | 1/2009 | Bareket et al. | 356/326 |

\* cited by examiner

*Primary Examiner* — Layla Lauchman  
(74) *Attorney, Agent, or Firm* — Suiter Swantz pc llo

(57) ABSTRACT

A spectroscopic system may include: a spectroscopic scatterometer; an angular-resolved spectrometer; and a fiber bundle having a two-dimensional input surface and a one-dimensional output surface.

19 Claims, 8 Drawing Sheets

ANGULAR RESOLVED SPECTROSCOPIC SCATTEROMETER

TECHNICAL FIELD

The following disclosures are related to devices and methods for metrology.

BACKGROUND

Existing scatterometry analysis methodologies include single-angle spectroscopic ellipsometry (SE-SA) and reflectometry (SR-SA), angular-resolved reflectometry (R-AR), and mechanical-scanning-over-angles SE (SE-scan). SE-SA systems may employ rotating-polarizer (RPE), rotating analyzer (RAE), or rotating compensator (RCE) configurations. Output from a SE-SA and SR-SA systems may merge signals from different angle-of incidence (AOI) and azimuth (Az) angles (e.g. via a numerical aperture (NA) integration process) and send the combined light beam into a spectrometer to produce a time-varying spectra. Those spectra in turn can be used to calculate polarization and reflectivity parameters.

SE-SA and SR-SA may result in a loss of information during NA integration. Angular-resolved reflectometry may be incapable of providing sufficient spectroscopic information. Mechanical-scanning-over-angles SE involves mechanically moving parts of the system to perform measurements at multiple angles with detrimental impact on time of measurements.

SUMMARY

An angular resolved spectroscopic scatterometer system and method disclosed.

A spectroscopic system may include: a spectroscopic ellipsometer and/or reflectometer with the ability to measure polarization and/or reflectivity properties of scattered light and more generally some or all of the Mueller matrix elements; an angular-resolved spectrometer; and a fiber bundle having a two-dimensional input surface and a one-dimensional output surface.

A method may include: generating a two-dimensional spectrographic scatterometry image; translating the two-dimensional spectrographic scatterometry image to a 1-dimensional spectrographic ellipsometry image; providing the 1-dimensional spectrographic scatterometry image to an angularly resolved spectrometer; and resolving the 1-dimensional spectrographic scatterometry image into component wavelengths.

BRIEF DESCRIPTION OF THE DRAWINGS

The numerous advantages of the disclosure may be better understood by those skilled in the art by reference to the accompanying figures in which FIG..

DETAILED DESCRIPTION OF THE INVENTION

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention. Reference will now be made in detail to the subject matter disclosed, which is illustrated in the accompanying drawings.

Figure 1:
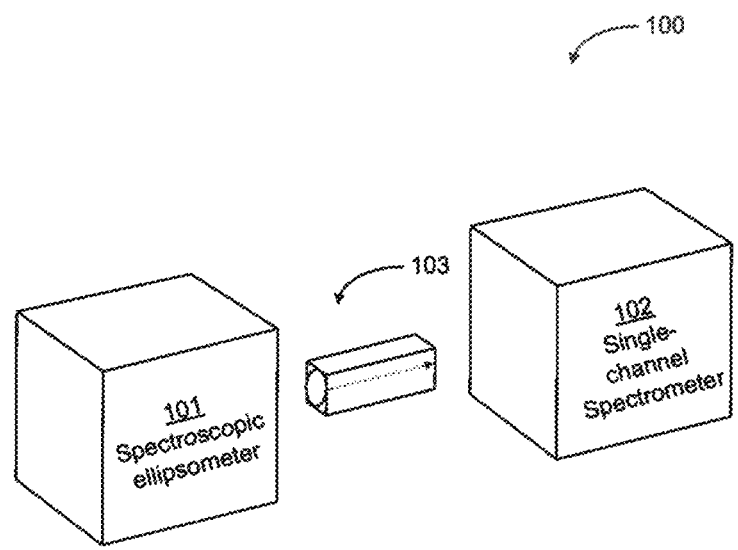
FIG. 1 depicts a high-level block diagram of a single-angle spectroscopic ellipsometer.

Referring to FIG. 1, a single-angle spectroscopic ellipsometer 100 is shown. The single-angle spectroscopic ellipsometer 100 may include a spectroscopic ellipsometer 101 and a single-channel spectrometer 102. The output of the spectroscopic ellipsometer 101 be a two-dimensional (2D) image which may be provided to a 2D fiber bundle 103. The 2D fiber bundle 103 may transmit the 2D image to the single-channel spectrometer 102 for further processing.

Figure 2:
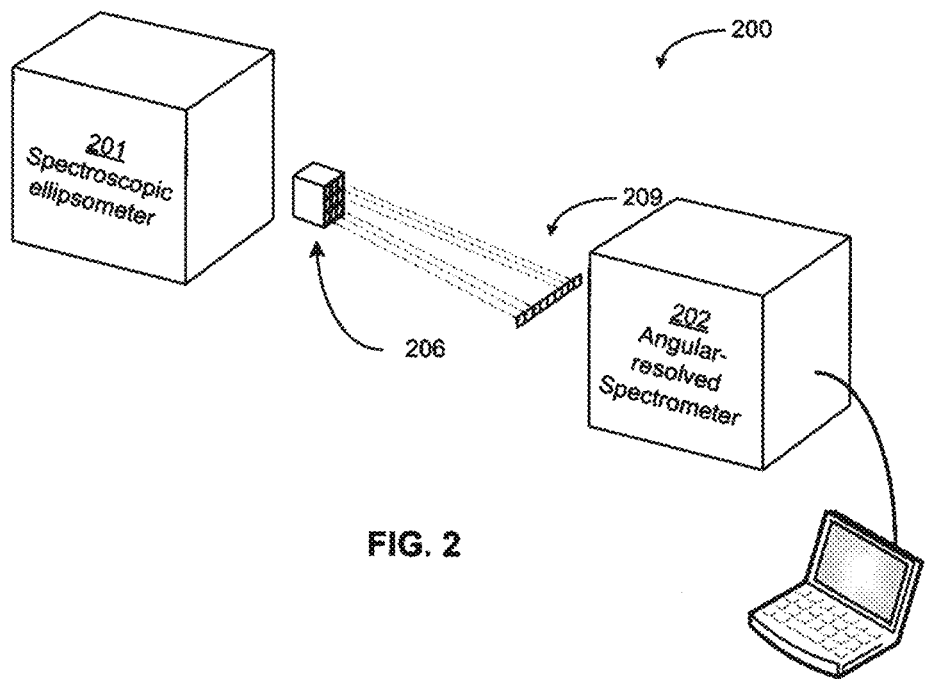
FIG. 2 depicts a high-level block diagram of an angular resolved spectroscopic ellipsometer.

Referring to FIG. 2, an angular-resolved spectroscopic ellipsometer 200 is shown. The angular-resolved spectroscopic ellipsometer 200 may include a spectroscopic ellipsometer 201 and an angularly resolved spectrometer 202. The angular-resolved spectroscopic ellipsometer 200 may be linked to a computing device configured to analyze data generated by the angular-resolved spectroscopic ellipsometer 200.

Figure 3:
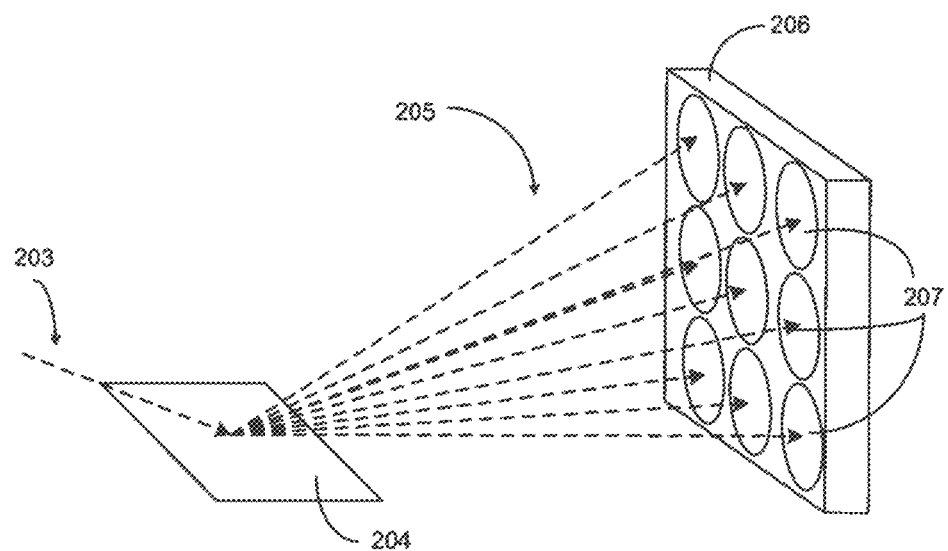
FIG. 3 depicts operation of a spectroscopic ellipsometer spectrometer.
Figure 4:
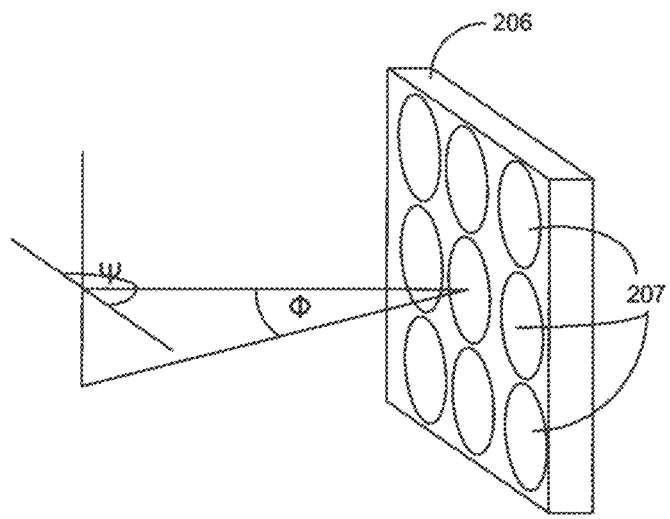
FIG. 4 depicts angles of incidence and azimuth angles relative to a fiber bundle.

Referring to FIG. 3, the spectroscopic ellipsometer 201 may direct a sampling beam 203 towards a spectroscopic ellipsometry target 204. Upon interaction with the target 204, the sampling beam 203 may be scattered at various angles associated with the surface of the target 204. As shown in FIG. 4, the reflected beams 205 may each have an angle of incidence $\phi$ and an azimuth angle $\psi$ relative to an input surface 206 including multiple fiber channels 207.

Referring again to FIG. 3, the output of the spectroscopic ellipsometer 201 may be a 2D image including multiple channels each associated with an angle-of-incidence/azimuth angle (AOI/Az) pair.

Figure 5:
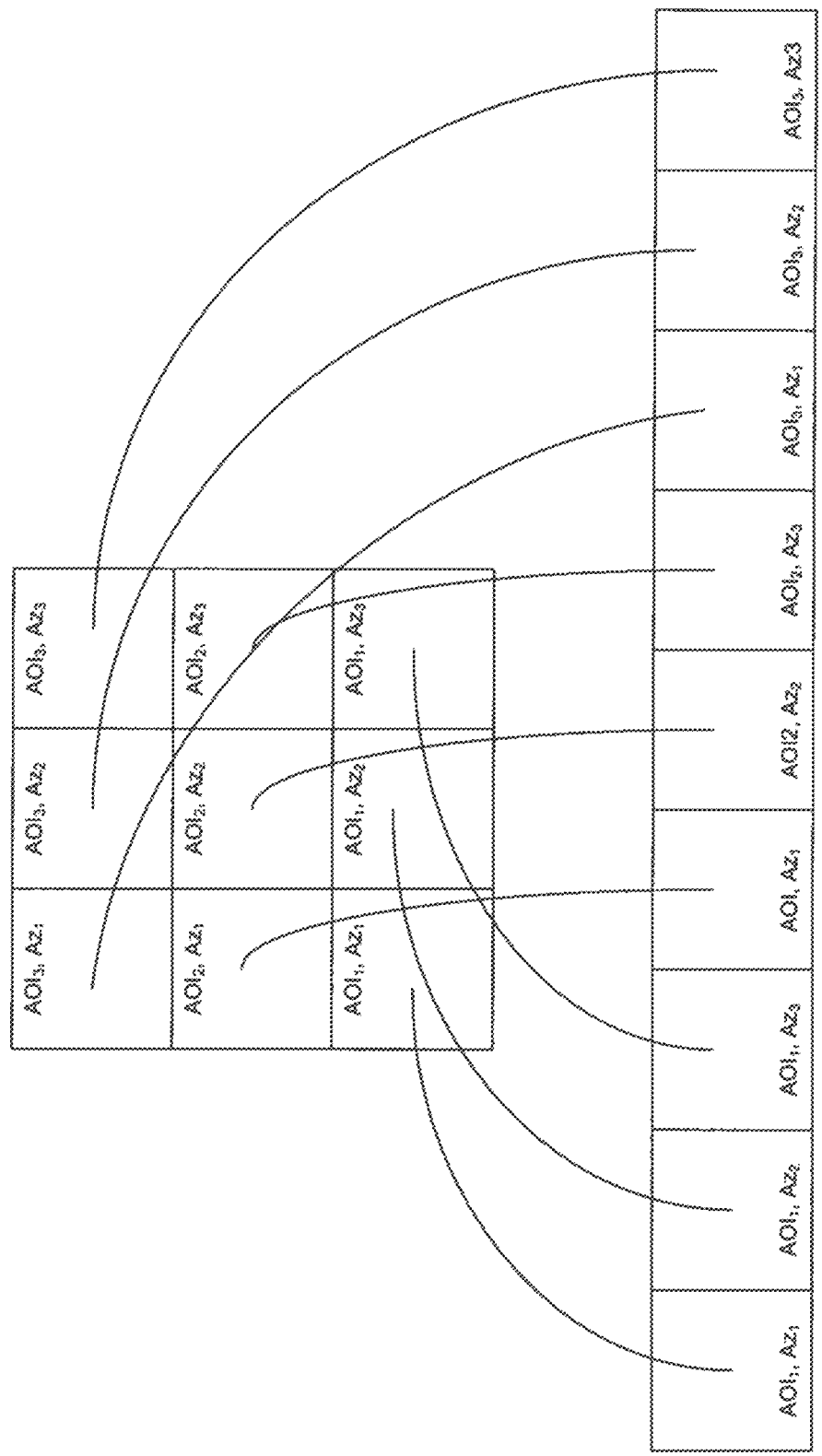
FIG. 5 depicts a 2D-to-1D mapping of spectroscopic ellipsometer channels.

Referring again to FIG. 2, the 2D image imparted on the input surface 206 may be provided to a 2D-to-1D mapping fiber bundle 208. The 2D-to-1D mapping fiber bundle 208 may translate the 2D image into a one-dimensional (1D) image to be provided to a 1D entrance slot 209 in the angularly resolved spectrometer 202. For example, the 2D image components may be translated to a 1D image according to the respective AOI/Az pair coordinates as shown in FIG. 5. The angularly resolved spectrometer 202 may then process the 1D image as will be described below.

Figure 6:
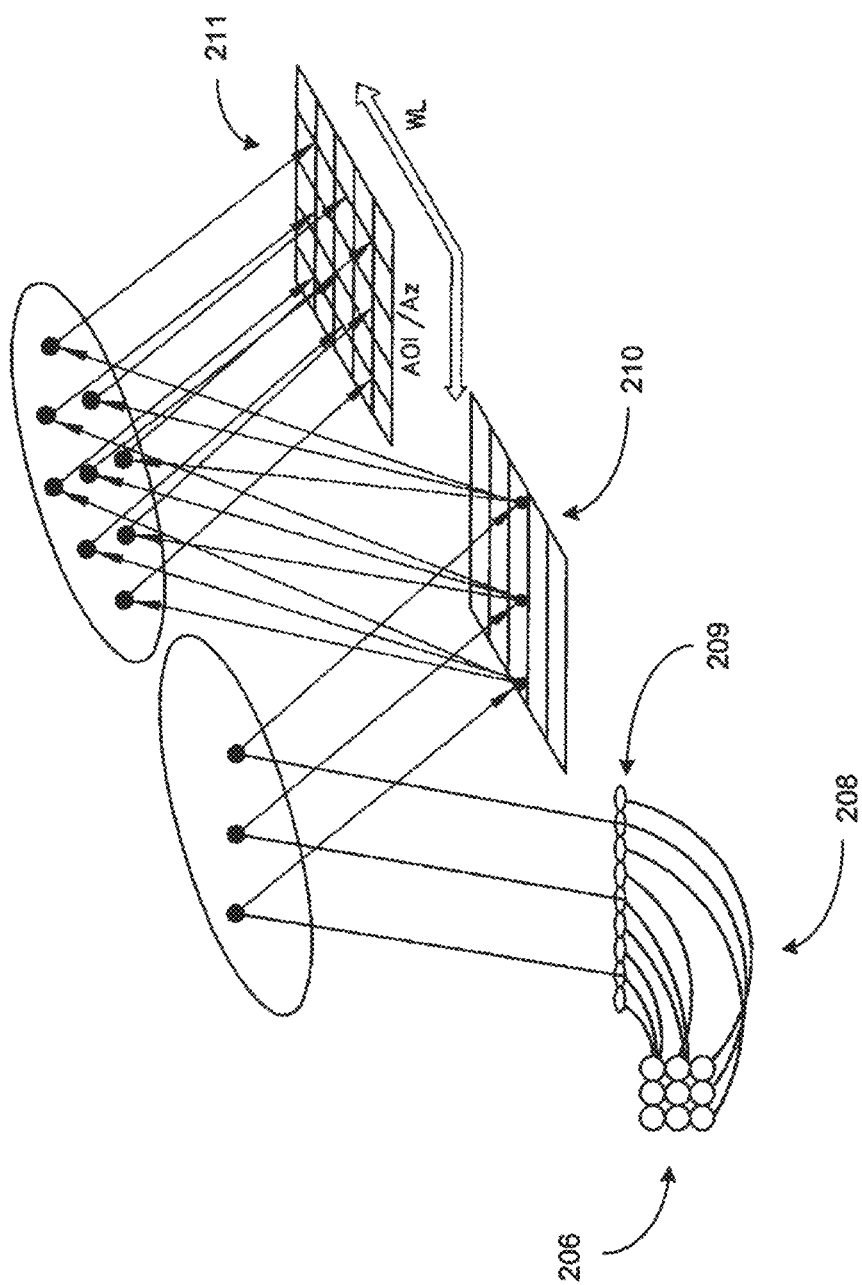
FIG. 6 depicts components of an angular resolved spectrometer.

Referring to FIG. 6, further detail regarding the various components of the angular-resolved spectroscopic ellipsometer 200 are shown. The angularly resolved spectrometer 202 may resolve wavelengths, as well as intensity changes along the 1D entrance slot 209. The 1D entrance slot 209 may illuminate a diffraction grating/prism 210 to spectrally resolve the input 1D image. A resulting spectrally-resolved pattern may be propagated to a 2D charged-coupled device 211 positioned in the image pathway. In one dimension of the 2D charged-coupled device 211 spectral intensity data may be stored according to wavelength. In a second dimension of the 2D charged-coupled device 211 spectral intensity data may be stored according to AOI/Az values.

In such a system, multiple output spectra may be generated. Each spectra may correspond to a different AOI/Az angle pair. Those spectra may be processed to generate complex polarization and/or reflectivity spectra, as well as derivatives of complex polarization and/or reflectivity spectra with respect to AOI and/or Az, thereby providing multiple independent channels of information as a function of time. Alternatively complex polarization and reflectivity at corresponding (AOI, Az) angles may be used directly. For each channel, corresponding complex polarization and reflectivity quantities may be calculated. Associated modeling software may also take into consideration AOI/Az-based derivatives of ellipsometric and/or reflectivity spectra.

In the analysis of SE output signals, various metrics may be used. Metrics may include values $\alpha$ and $\beta$ representing first and second harmonics of a given output signal of an SE. The angular-resolved spectroscopic ellipsometer 200 may provide angularly resolved signals (e.g. resolved by Az or AOI angles) where $\alpha$ and $\beta$ may be computed for a particular Az/AOI channel.

If Az or AOI angles are separated far enough (e.g. high enough sensitivity) it may effectively create independent channels to break correlations across various parameters.

Figure 7:
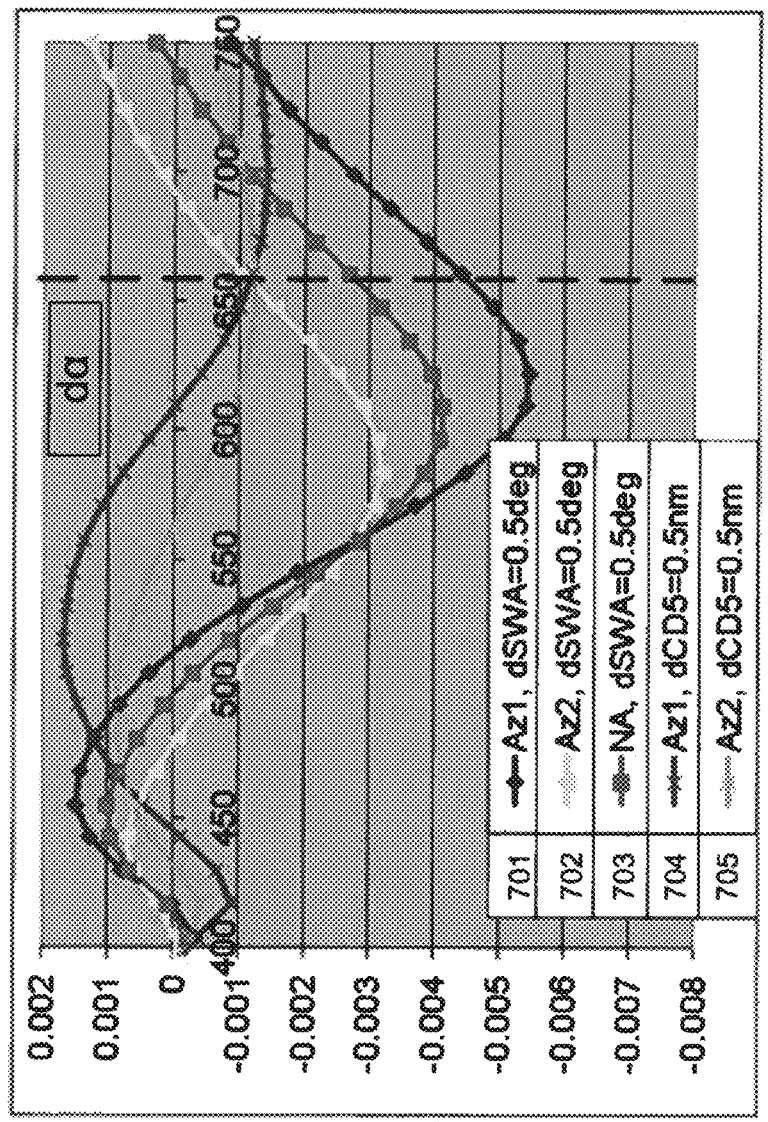
FIG. 7 depicts plots of spectroscopic spectra.

Referring to FIG. 7 various exemplary spectra are shown for a spectroscopic target having various structural dimensions (e.g. sidewall angle or critical distance). A spectra 701 illustrates a sensitivity of the $\alpha$ parameter (i.e. $d\alpha$) to a change in sidewall angle (e.g. a change of 0.5 degrees) for a target measured at a first azimuth angle Az1 relative to the target across a spectrum of wavelengths between 400 and 750 nm. A spectra 702 illustrates a sensitivity of the a parameter to a change in sidewall angle (e.g. a change of 0.5 degrees) for a target measured at a second azimuth angle Az2 relative to the target across the spectrum. A spectra 703 illustrates a numerical aperture (NA) average (as may be determined from standard non-angular resolved spectroscopic ellipsometer without regard to azimuth angle influence) of the sensitivity of the $\alpha$ parameter to a change in sidewall angle (e.g. a change of 0.5 degrees) across the spectrum. A spectra 704 illustrates a sensitivity of the $\alpha$ parameter to a change in critical distance (e.g. a change of 0.5 nm) for a target measured at the first azimuth angle Az1 relative to the target across a spectrum of wavelengths between 400 and 750 nm. A spectra 705 illustrates a sensitivity of the a parameter to a change in critical distance (e.g. a change of 0.5 nm) for a target measured at the second azimuth angle Az2 relative to the target across the spectrum.

As can be seen in FIG. 7, at a wavelength of 660 nm, for the NA average channel, a change of 0.5 deg change in sidewall angle is results in a −0.0027 change in $\alpha$. Also, at a wavelength of 660 nm, a change of critical distance of 0.5 nm results in a −0.0012 change in $\alpha$. As such, assuming a linear relationships between a for sidewall angle and critical distance, when utilizing an NA average channel for computations at 660 nm, the relative contributions to a sensitivity of change in sidewall angle of 0.5 degrees and a change in critical distance of 1.125 nm (i.e. (−0.0027/−0.0012)×0.5) could not be differentiated as each would result in a change in $\alpha$ of −0.0027.

The use of an differential values at various azimuth angles may be used to break such correlations. An differential may be computed as follows for sidewall angle (SWA) and critical distance (CD):

$$\frac{d\ \alpha(SWA, Az_1) - d\ \alpha(SWA, Az_2)}{2} \quad \frac{d\ \alpha(CD, Az_1) - d\ \alpha(CD, Az_2)}{2}$$

For example, as shown FIG. 7, for a sidewall angle change of 0.5 degrees, the differential will be approximately 0.003. For a critical distance change of 0.5 nm, the differential will be approximately 0. As such, the relative contributions to a sensitivity can more accurately determined, thereby breaking the correlation described above.

Following is a description of a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 8:
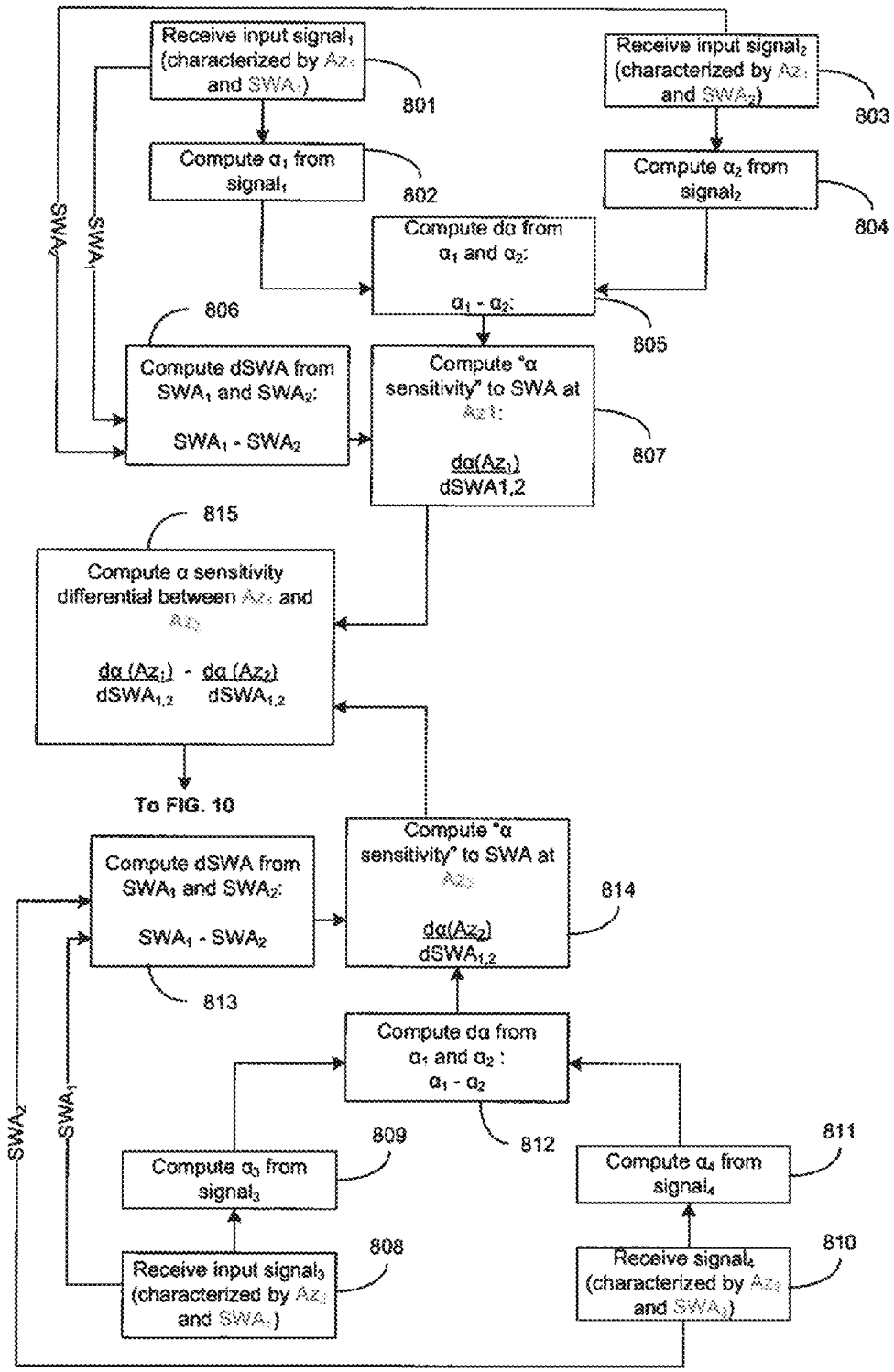
FIG. 8 depicts a method for analyzing angularly resolved spectroscopic ellipsometer signals.
Figure 9:
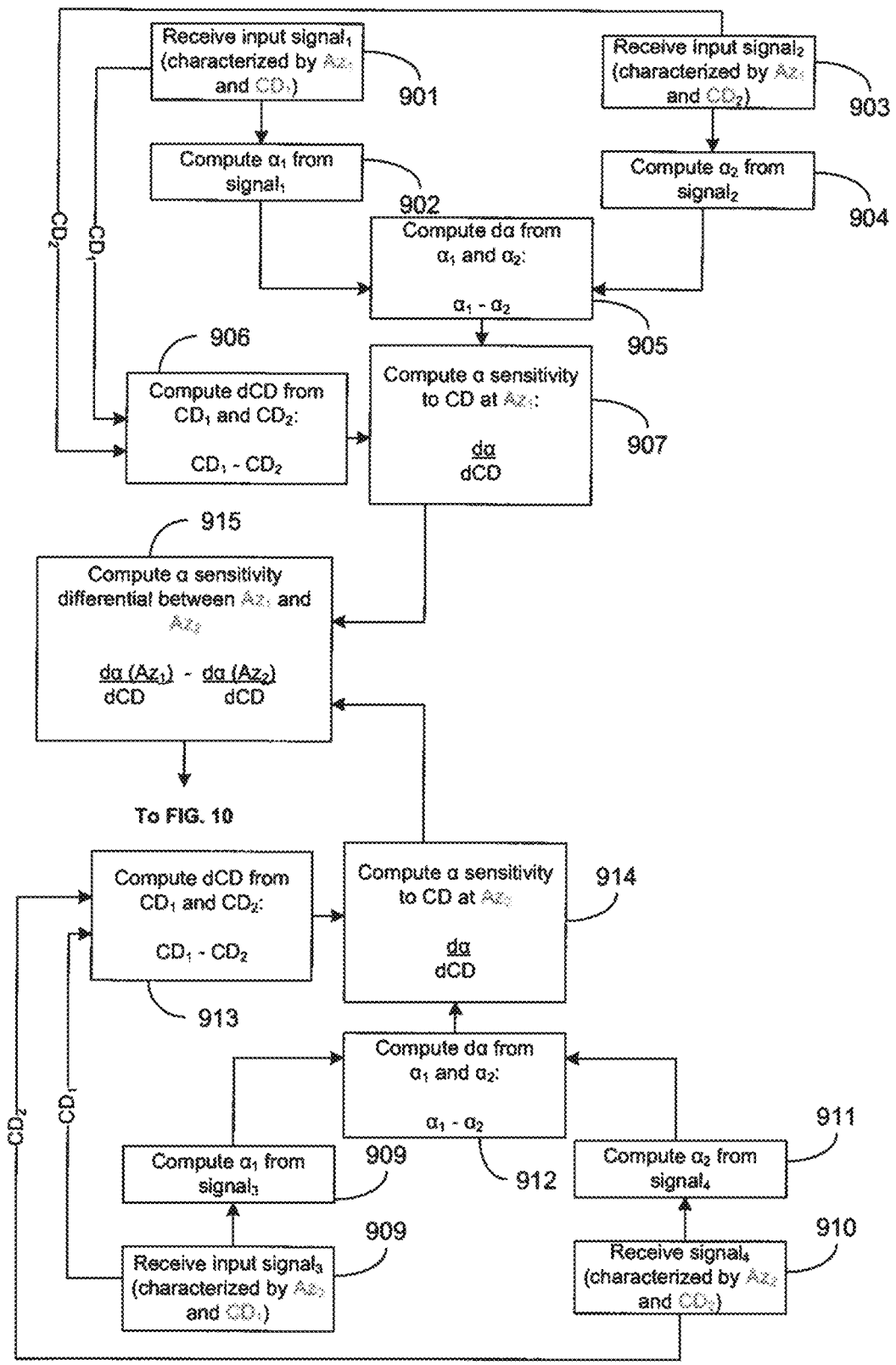
FIG. 9 depicts a method for analyzing angularly resolved spectroscopic ellipsometer signals.
Figure 10:
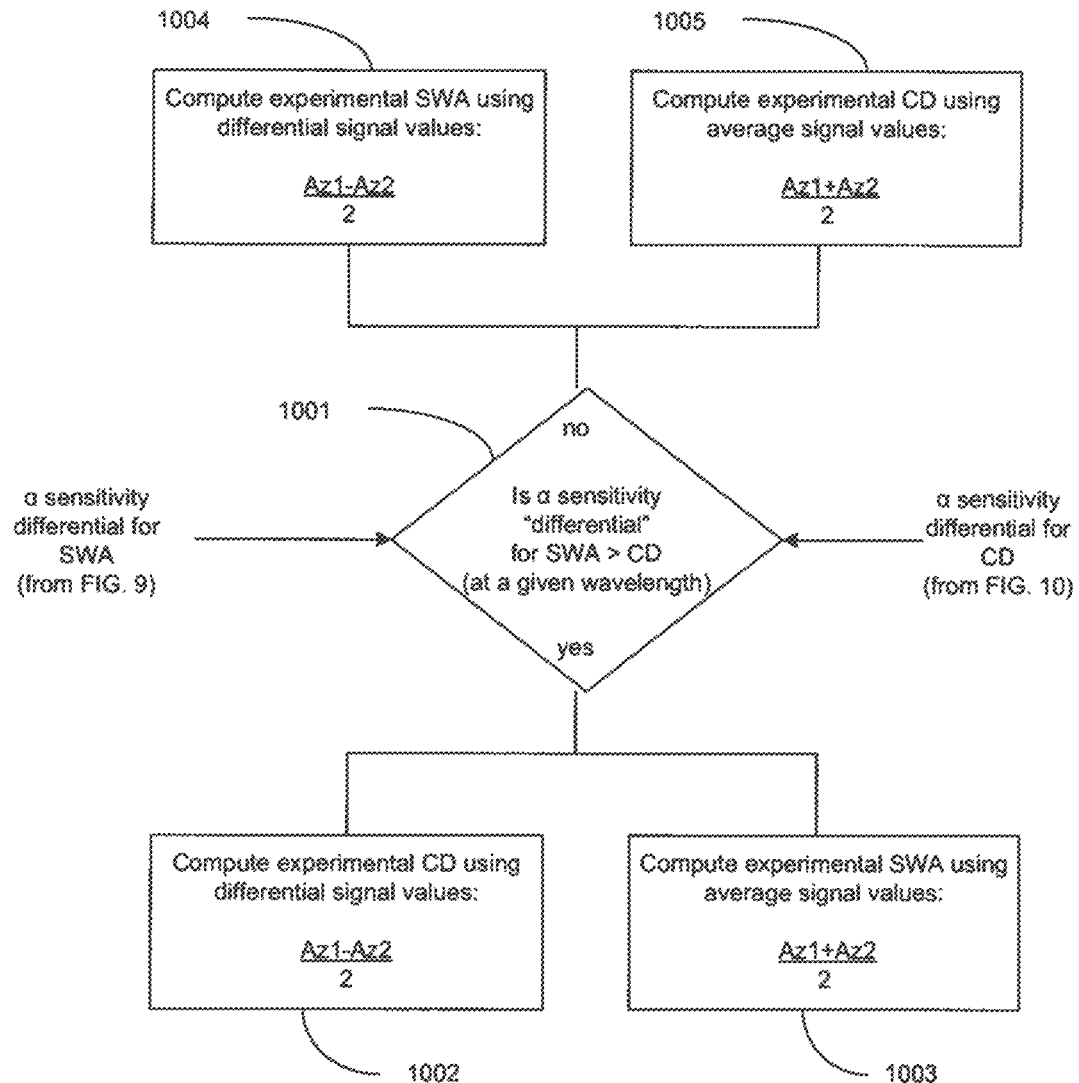
FIG. 10 depicts a method for analyzing angularly resolved spectroscopic ellipsometer signals.

FIGS. 8-10 illustrate an operational flow representing example operations related to breaking correlations between sidewall angle and critical distance in scatterometry measurements. In FIGS. 8-10 that include various examples of operational flows, discussion and explanation may be provided with respect to the above-described examples of FIGS. 1-7, and/or with respect to other examples and contexts. However, it should be understood that the operational flows may be executed in a number of other environments and contexts, and/or in modified versions of FIGS. 8-10. In addition, although the various operational flows are presented in the sequence(s) illustrated, it should be understood that the various operations may be performed in other orders than those that are illustrated, or may be performed concurrently.

Referring to FIG. 8, at an operation 801, a scatterometry signal$_1$ characterized by an azimuth angle Az$_1$ with respect to a scatterometry target having a sidewall angle SWA$_1$ may be received. For example, as shown in FIGS. 1-7, a sampling beam 203 may be scattered at various angles associated with the surface of the target 204 towards the input surface 206 of the 2D-to-1D mapping fiber bundle 208. A channel of the 2D-to-1D mapping fiber bundle 208 associated with the azimuth angle Az$_1$ may provide the signal$_1$ to the angularly resolved spectrometer 202 which may resolve the signal$_1$ into its component wavelengths which may be projected on the 2D charged-coupled device 211 for detection.

At operations 803, 808 and 810, a scatterometry signal$_2$ characterized by an azimuth angle Az$_1$ with respect to a scatterometry target having a sidewall angle SWA$_2$, a scatterometry signal$_3$ characterized by an azimuth angle Az$_2$ with respect to a scatterometry target having a sidewall angle SWA$_1$, and a scatterometry signal$_4$ characterized by an azimuth angle Az$_2$ with respect to a scatterometry target having a sidewall angle SWA$_2$ may be received in a similar manner as signal$_1$ as described above.

At operations 802, 804, 809 and 811 upon detection the signal$_1$, signal$_2$, signal$_3$ and signal$_4$, an associated scatterometry quantity a may be calculated for each of signal$_1$, signal$_2$, signal$_3$ and signal$_4$. The value of $\alpha$ may be a vector-valued function of elements of a Mueller matrix of a sample being measured, and represent polarization and/or reflectivity properties.

At operation 805, a change in α between signal$_1$ and signal$_2$ (dα$_{1,2}$) resulting from a difference in SWA$_1$ and SWA$_2$ may be computed. At operation 806, the difference between SWA$_1$ and SWA$_2$ (dSWA$_{1,2}$) may be computed. At operation 807, a sensitivity of α to the change in SWA determined at azimuth angle Az$_1$ (dαAz$_1$) may be computed.

At operation 812, a change in a between signal$_3$ and signal$_4$ (dα$_{3,4}$) resulting from a difference in SWA$_1$ and SWA$_2$ may be computed. At operation 813, the difference between SWA$_1$ and SWA$_2$ (dSWA$_{1,2}$) is computed. At operation 814, a sensitivity of α to the change in SWA determined at azimuth angle Az$_2$ (dαAz$_2$) may be computed.

At operation 815, an α sensitivity differential between dαAz$_1$ and dαAz$_2$ the may be computed.

Referring to FIG. 9, at an operation 901, a scatterometry signal$_1$ characterized by an azimuth angle Az$_1$ with respect to a scatterometry target having a critical distance CD$_1$ may be received. For example, as shown in FIGS. 1-7, a sampling beam 203 may be scattered at various angles associated with the surface of the target 204 towards the input surface 206 of the 2D-to-1D mapping fiber bundle 208. A channel of the 2D-to-1D mapping fiber bundle 208 associated with the azimuth angle Az$_1$ may provide the signal$_1$ to the angularly resolved spectrometer 202 which may resolve the signal$_1$ into its component wavelengths which may be projected on the 2D charged-coupled device 211 for detection.

At operations 903, 908 and 910, a scatterometry signal$_2$ characterized by an azimuth angle Az$_1$ with respect to a scatterometry target having a sidewall angle CD$_2$, a scatterometry signal$_3$ characterized by an azimuth angle Az$_2$ with respect to a scatterometry target having a sidewall angle CD$_1$, and a scatterometry signal$_4$ characterized by an azimuth angle Az$_2$ with respect to a scatterometry target having a sidewall angle CD$_2$ may be received in a similar manner as signal$_1$ as described above.

At operations 902, 904, 909 and 911 upon detection the signal$_1$, signal$_2$, signal$_3$ and signal$_4$, an associated a may be calculated for each of signal$_1$, signal$_2$, signal$_3$ and signal$_4$.

At operation 905, a change in a between signal$_1$ and signal$_2$ (dα$_{1,2}$) resulting from a difference between CD$_1$ and CD$_2$ may be computed. At operation 906, the difference between CD$_1$ and CD$_2$ (dCD$_{1,2}$) may be computed. At operation 907, a sensitivity of a to the change in CD determined at azimuth angle Az$_1$ (dαAz$_1$) may be computed.

At operation 912, a change in a between signal$_3$ and signal$_4$ (dα$_{3,4}$) resulting from a difference between CD$_1$ and CD$_2$ may be computed. At operation 913, the difference between CD$_1$ and CD$_2$ (dCD$_{1,2}$) is computed. At operation 914, a sensitivity of a to the change in CD determined at azimuth angle Az$_2$ (dαAz$_2$) may be computed.

At operation 915, an α sensitivity differential between dαAz$_1$ and dαAz$_2$ the may be computed.

Referring to FIG. 10, at an operation 1001, the sensitivity differential associated with sidewall angle (as computed at operation 815) at a given wavelength and the sensitivity differential associated with critical distance (as computed at operation 915) at the wavelength are compared.

If the sensitivity differential associated with sidewall angle is greater than the sensitivity differential associated with critical distance, experimental (e.g. reported by the metrology instrument) critical distances may be computed using differential values determined from respective azimuth channels (see operation 1002) while experimental sidewall angles may be computed using average values determined from the respective azimuth channels (see operation 1003).

If the sensitivity differential associated with sidewall angle is less than the sensitivity differential associated with critical distance, experimental (e.g. reported by the metrology instrument) sidewall angles may be computed using differential values determined from respective azimuth channels (see operation 1004) while experimental critical distances may be computed using average values determined from the respective azimuth channels (see operation 1005).

It will be noted that the operations of FIGS. 8-10 may be modified to incorporate angle of incidence (AOI) parameters in place of azimuth angle parameters to provide yet another level of resolution for breaking correlations in the scatterometry data.

In the present disclosure, the methods disclosed may be implemented as sets of instructions or software readable by a device embodied in a tangible media, such as memory. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A spectroscopic system comprising:
a spectroscopic scatterometer;
an angular-resolved spectrometer; and
a fiber bundle having a two-dimensional input surface and a one-dimensional output surface.

2. The system of claim 1, wherein spectroscopic scatterometry signals generated by the spectroscopic scatterometer are provided to the two-dimensional input surface.

3. The system of claim 1, wherein spectroscopic scatterometry signals generated by the spectroscopic scatterometer are received by the two-dimensional input surface are translated to the one-dimensional output surface and provided as an input to the angular-resolved spectrometer.

4. The system of claim 3, wherein the angular-resolved spectrometer comprises:
a diffraction grating configured to resolve the one-dimensional input into component wavelength signals; and
a two-dimensional detector having:
a first axis associated with a wavelength spectrum; and
a second axis associated with an azimuth angle/angle of incidence pair of the two-dimensional input surface of the fiber bundle.

5. The system of claim 1, wherein the spectroscopic scatterometer comprises: a spectroscopic ellipsometer.

6. The system of claim 1, wherein the spectroscopic scatterometer comprises: a spectroscopic reflectometer.

7. A method comprising:
generating a two-dimensional spectrographic scatterometry image;
mapping the two-dimensional spectrographic scatterometry image to a 1-dimensional spectrographic ellipsometry image;
providing the 1-dimensional spectrographic scatterometry image to an angularly resolved spectrometer; and
resolving the 1-dimensional spectrographic scatterometry image into component wavelengths.

8. A method for performing scatterometry comprising:
directing one or more reference beams at a scatterometry target;
receiving one or more scatterometry signals having a characteristic azimuth angle and angle of incidence relative to the scatterometry target with a two-dimensional array of fibers;
translating the two-dimensional array of fibers to a one-dimensional segment of fibers;
providing the output of the one-dimensional segment of fibers as an input to an angular resolved spectrometer;
resolving the input of the angular resolved spectrometer into signals associated with the component wavelengths of each channel of the input;
providing the component wavelength-resolved signals to a two-dimensional detector having;
a first axis associated with a wavelength spectrum; and
a second axis associated with an azimuth angle/angle of incidence pair of the two-dimensional array of fibers.

9. A computer-implemented method for breaking scatterometry correlations resulting from multiple spectrographic target dimensions comprising:
computing a first sensitivity difference between a sensitivity of a scatterometry parameter to a change in a first target dimension detected at a first angle and a sensitivity of the scatterometry parameter to a change in the first target dimension detected at a second angle;
computing a second sensitivity difference between a sensitivity of the scatterometry parameter to a change in a second target dimension at the first angle and a sensitivity of the scatterometry parameter to a change in the second target dimension at the second angle; and
comparing the first sensitivity difference to the second sensitivity difference;
computing a value of the first dimension for a scatterometry target and
a value of the second dimension for the scatterometry target according to the comparison with a processing device.

10. The method of claim 9, wherein computing a first sensitivity difference between a sensitivity of a scatterometry parameter to a change in a first dimension detected at a first angle and a sensitivity of the scatterometry parameter to a change in the first target dimension detected at a second angle comprises:
computing a scatterometry parameter from a scatterometry signal received at a first angle with respect to a spectrographic target having a first value of the first target dimension;
computing a scatterometry parameter from a scatterometry signal received at the first azimuth angle with respect to a spectrographic target having a second value of the first target dimension;
computing a sensitivity of the scatterometry parameter to a change in the first target dimension at the first angle;

computing a scatterometry parameter from a scatterometry signal received at a second angle with respect to a spectrographic target having a third value of the first target dimension;

computing a scatterometry parameter from a scatterometry signal received at the second angle with respect to a spectrographic target having a fourth value of the first target dimension; and computing a sensitivity of the scatterometry parameter to a change in the first target dimension at the second angle.

11. The method of claim 9, wherein the computing a second sensitivity difference between a sensitivity of the scatterometry parameter to a change in a second target dimension at the first angle and a sensitivity of the scatterometry parameter to a change in the second target dimension at the second angle comprises:

computing the scatterometry parameter from a scatterometry signal received at a first azimuth angle with respect to a spectrographic target having a first value of the second dimension;

computing the scatterometry parameter from a scatterometry signal received at the first azimuth angle with respect to a spectrographic target having a second value of the second dimension;

computing a sensitivity of the scatterometry parameter to a change in the second dimension at the first azimuth angle;

computing the scatterometry parameter from a scatterometry signal received at a second azimuth angle with respect to a spectrographic target having a third value of the second dimension;

computing the scatterometry parameter from a scatterometry signal received a the second azimuth angle with respect to a spectrographic target having a fourth value of the second dimension; and computing a sensitivity of the scatterometry parameter to a change in the second dimension at the second azimuth angle;

computing a value of the first dimension for a scatterometry target according to the comparison; and computing a value of the second dimension for the scatterometry target according to the comparison.

12. The method of claim 9, wherein computing a value of the first dimension for a scatterometry target according to the comparison comprises:

computing a value associated with the first target dimension using an differential of a signal obtained at the first angle and a signal obtained at a second angle when the second sensitivity difference is greater than the first sensitivity difference.

13. The method of claim 9, wherein computing a value of the second dimension for the scatterometry target according to the comparison comprises:

computing a value associated with the second dimension using an average of a signal obtained at the first angle and a signal obtained at a second angle when the second sensitivity difference is greater than the first sensitivity difference.

14. The method of claim 9, wherein computing a value of the first dimension for a scatterometry target according to the comparison comprises:

computing a value associated with the first dimension using an average of a signal obtained at the first angle and a signal obtained at a second angle when the second sensitivity difference is less than the first sensitivity difference.

15. The method of claim 9, wherein computing a value of the second dimension for the scatterometry target according to the comparison comprises:

computing a value associated with the second dimension using a differential of a signal obtained at the first angle and a signal obtained at a azimuth angle when the second sensitivity difference is less than the first sensitivity difference.

16. The method of claim 9, wherein the first dimension is a sidewall angle.

17. The method of claim 9, wherein the second dimension is a critical distance.

18. The method of claim 9, wherein the first angle and second angle are azimuth angles.

19. The method of claim 9, wherein the first angle and second angle are angles of incidence.

* * * * *